United States Patent [19]

Selkoe

[11] Patent Number: 5,262,332
[45] Date of Patent: Nov. 16, 1993

[54] DIAGNOSTIC METHOD FOR ALZHEIMER'S DISEASE: EXAMINATION OF NON-NEURAL TISSUE

[75] Inventor: Dennis J. Selkoe, Jamaica Plain, Mass.

[73] Assignee: Brigham and Women's Hospital, Boston, Mass.

[21] Appl. No.: 410,138

[22] Filed: Sep. 19, 1989

Related U.S. Application Data

[63] Continuation-in-part of Ser. No. 333,609, Apr. 5, 1989, abandoned.

[51] Int. Cl.$^5$ .................. G01N 33/53; G01N 33/543
[52] U.S. Cl. .................................. 436/518; 435/7.1; 435/7.9; 435/960; 435/967; 436/501; 436/547; 436/548; 436/63; 436/174; 436/811
[58] Field of Search ............... 436/501, 518, 536, 547, 436/548, 63, 177, 808, 811, 164; 530/387, 388.1, 389.1; 435/7.9, 7.1, 960, 967

[56] References Cited

U.S. PATENT DOCUMENTS 4,584,278  4/1986  Knauf .................................. 436/825
4,666,829  5/1987  Glenner et al. ..................... 435/6

OTHER PUBLICATIONS

Majocha et al., Proc. Nat'l. Acad. Sci. (USA), vol. 85, pp. 6182–6186 (Aug. 1988).
Baker et al., Age, vol. 11, pp. 60–65 (1988).
Roher et al., Proc. Natl. Acad. Sci. (USA), vol. 83, pp. 2662–2666 (Apr. 1986).
Glenner, G. G., Cell, vol. 52, pp. 307–308 (Feb. 12, 1988).
Joachim, et al., Nature, vol. 341, pp. 226–230 (Sep. 21, 1989).
Mark, J., Science, vol. 249, pp. 984–985 (Aug. 31, 1990).
"Tracking Alzheimer's: Tangles in Brain Cells Believed to Hold Key", The Washington Post, Feb. 25, 1991, p. 1A3.
Barrow, C., et al., "Solution Structures of $\beta$ Peptide and its Constituent Fragments: Relation to Amyloid Deposition," Science 253:179–182 (1991).
Burdick, D., et al., "Assembly and Aggregation Properties of Synthetic Alzheimer's A4/$\beta$ Amyloid Peptide Analogs," J. Biol. Chem. 267:546–554.
Giaccone, G., et al., "Down Patients: Excellular Preamyloid Deposits Precede Neuritic Degeneration and Senile Plaques," Neurosci. Lett. 97:232–238 (1989).
Glenner, G., "The Proteins and Genes of Alzheimer's Disease," Biomed. & Pharmacother. 42:579–584 (1988).
Glenner, G., et al., "Alzheimer's Disease and Down's Syndrome: Sharing of a Unique Cerebrovascular Amyloid Fibril Protein," Biochem. Biophys. Res. Comm. 122:1131–1135 (1984).
Goate, A., et al., "Segregation of a Missense Mutation in the Amyloid Precursor Protein Gene with Familial Alzheimer's Disease," Nature 349:704–706 (1991).
Hardy, J. A., et al., "Alzheimer's Disease: The Amyloid Cascade Hypothesis," Science 256:184–185 (1992).

(List continued on next page.)

Primary Examiner—Esther L. Kepplinger
Assistant Examiner—Carol E. Bidwell
Attorney, Agent, or Firm—Lyon & Lyon

[57] ABSTRACT

This invention provides a method as well as a kit for diagnosing Alzheimer's disease. The method comprises the steps of obtaining a non-neural tissue biopsy sample, contacting at least a portion of the sample with a quantity of antibodies capable of identifying $\beta$AP, a $\beta$-amyloid precursor protein fragment comprising $\beta$AP, or a $\beta$AP peptide fragment of about 8 or more amino acids sufficient to allow detection of said protein, protein fragment or peptide fragment, and monitoring the extent of the reaction between the sample and the antibodies. The kit comprises antibodies specific for $\beta$-amyloid protein, or a $\beta$-amyloid precursor protein fragment comprising $\beta$-amyloid protein, or a peptide fragment of $\beta$-amyloid protein of at least about eight amino acids, and a means for detecting the extent of the reaction of the antibodies with a non-neural tissue sample.

20 Claims, No Drawings

OTHER PUBLICATIONS

Hilbich, C., "Aggregation and Secondary Structure of Synthetic Amyloid βA4 Peptides of Alzheimer's Disease," J. Mol. Biol. 218:149–163 (1991).

Joachim, C. L., "Protein Chemical and Immunocytochemical Studies of Meningovascular β-Amyloid Protein in Alzheimer's Disease and Normal Aging," Brain Res. 474:100–111 (1988).

Khachaturian, Z. S., "Diagnosis of Alzheimer's Disease," Arch. Neurol. 42:1097–1105 (1985).

Kislevsky, R., "From Alzheimer's Disease: Current Concepts on the Pathogenesis of Amyloidosis," Can. J. Physiol. Pharmacol. 65:1805–1815 (1987).

Kosik, K. S., et al., "Mirotubule–Associated Protein Tau is a Major Antigenic Component of Paired Helical Filaments in Alzheimer Disease," Proc. Natl. Acad. Sci. 83:4044–4048 (1986).

Lee, V. M.-Y, et al., "A Major Subunit of Paired Helical Filaments and Derivatized Forms of Normal Tau," Science 251:675–678 (1991).

Lucotte, G., et al., "Alzheimer's Mutation," Nature 351:530 (1991).

Masters, C. L., et al., "Amyloid Plaque Core Protein in Alzheimer Disease and Down Syndrome," Proc. Natl. Acad Sci. 82:4245–4249 (1985).

McKhann, G., et al., "Clinical Diagnosis of Alzheimer's Disease," Neurology 34:939–944 (1984).

Murrell, J., et al., "A Mutation in the Amyloid Precursor Protein Associated with Hereditary Alzheimer's Disease," Science 254:97–99 (1991).

Naruse, S., et al., "Mis-Sense Mutation Val→Ile in Exon 17 of Amyloid Precursor Protein Gene in Japanese Familial Alzheimer's Disease," The Lancet 337:978–979 (1991).

Pardridge, W. M., et al., "High Molecular Weight Alzheimer's Disease Amyloid Peptide Immunoreactivity in Human Serum and CSF is an Immunoclobulin G," Biochem. Biophys. Res. Comm. 145:241–248 (1987).

Selkoe, D. J., "Amyloid Protein and Alzheimer's Disease," Sci. Am. Nov. 1991 pp. 68–78.

Selkoe, D. J., "The Molecular Pathology of Alzheimer's Disease," Neuron, 6:487–498 (1991).

Selkoe, D. J., et al., "Isolation of Low-Molecular–Weight Proteins from Amyloid Plaque Fibers in Alzheimer's Disease," J. Neurochem. 46:1820–1834 (1986).

Tanaka, T., et al., "Efficient Generation of Antibodies to Oncoproteins by Using Synthetic Peptide Antigens," Proc. Natl. Acad. Sci. 82:3400–3404.

Tanzi, R. E., et al., "Amyloid Beta-Protein Gene: cDNA, mRNA Distribution, and Genetic Linkage Near the Alzheimer Locus," Science 235:880–884 (1987).

DIAGNOSTIC METHOD FOR ALZHEIMER'S DISEASE: EXAMINATION OF NON-NEURAL TISSUE

This is a Continuation-in-Part of U.S. patent application Ser. No. 07/333,609, filed Apr. 5, 1989, now abandoned, and assigned to the assignee of the instant invention.

BACKGROUND OF THE INVENTION

1. Field of the Invention

The instant invention generally relates to the diagnosis and monitoring of Alzheimer's Disease.

Alzheimer's Disease (AD) is the most common cause of progressive intellectual failure in aged humans, and is typified by gradual neurological deterioration including memory loss, disorientation, and general intellectual regression. It eventually produces additional symptoms of physical deterioration, such as motor disability, incontinence and weight loss, and is often fatal. It has been observed in races and ethnic groups worldwide and presents a present and future major public health and economic problem. The disease is estimated to affect two to three million individuals in the United States alone.

The problem is compounded by substantial difficulties in making a definitive diagnosis of the disease during the patient's lifetime. Typically, Alzheimer's Disease is definitively diagnosed at autopsy, from an examination of the condition of the brain. Alzheimer's Disease is earmarked by structural changes in the form of filamentous lesions occurring in particular regions of the brain. These brain lesions are referred to as (1) senile (amyloid) plaques; (2) amyloid angiopathy (deposition of amyloid in small blood vessels); (3) neurofibrillary tangles; and (4) altered nerve cell fibers (neuritic dystrophy).

2. Background Art

The brains of virtually all very old humans contain at least some small quantities of the filamentous brain lesions which are characteristic of Alzheimer's Disease (AD) and occur within neurons (neurofibrillary tangles), in extracellular cerebral deposits (senile or amyloid plaques) and in meningeal and cerebral blood vessels (amyloid angiopathy). Chemical, immunochemical and molecular biological analyses during recent years have shown that a 4.2 kiloDalton (kDa) protein (of about 38 to about 43 amino acids), designated $\beta$-amyloid protein ($\beta$-AP) or A4, is a subunit of the vascular and cerebral amyloid filaments that occur in the brains of individuals with AD or with trisomy 21 (Down's syndrome), as well as (to a lesser extent) in individuals undergoing the normal aging process. See Glenner and Wong, Biochem. Biophys. Res. Commun. 120: 885–890 (1984); Glenner and Wong, Biochem. Biophys. Res. Commun. 122: 1131–1135 (1984); Masters et al., Proc. Natl. Acad. Sci. USA 82: 4245–4249 (1985); Selkoe et al., J. Neurochem. 46: 1820–1834 (1986); Kang et al., Nature 325: 733–736 (1987); and Coria et al., Am. J. Pathol. 129: 422–428 (1988). These analyses have also shown that the $\beta$-AP is a small fragment of a much larger precursor protein that is normally produced by cells in many tissues of various animals. The gene coding for this $\beta$-AP precursor protein in humans is located on the long arm of human chromosome 21.

The first purification and partial amino acid sequencing of the $\beta$-amyloid protein of AD was reported by Glenner and Wong in 1984 (Glenner and Wong, Biochem. Biophys. Res. Commun. 120: 885–890, (1984)). They isolated $\beta$-AP from the meningeal blood vessels of patients who died with AD, using a modification of a long-established protocol for purifying amyloids from tissues. They were able to establish the amino acid sequence of the first 28 amino acids of what was later shown to be a 38–43 amino acid protein. The isolation procedure that they used and their sequence data are described in U.S. Pat. No. 4,666,829 issued to Glenner et al. on May 19, 1987. In 1985, they made synthetic peptides including the first 10 amino acids of the 28-amino acid sequence identified by them. These synthetic peptides were then injected into either rabbits or mice to produce, respectively, polyclonal or monoclonal antibodies. These antibodies detected (i.e., reacted with) both the senile (amyloid) plaques and the vascular amyloid deposits in AD and normal aged brains.

PCT application having Int. Pub. No. WO 88/03951 assigned to California Biotechnology, Inc., is directed to certain DNA sequences encoding the $\beta$-amyloid precursor protein, and to the use of their recombinant proteins for generating antibodies for cerebrospinal fluid or serum diagnosis of Alzheimer's Disease.

Throughout the more than 80 years since Alzheimer's Disease was first identified as a disease, the pathological lesions of AD have been found only in the brain. Since the examination of a patient's brain tissue by biopsy is particularly invasive and, therefore, very rarely carried out, a need exists for an effective, less invasive diagnostic method that can be used simply and safely on a living subject.

SUMMARY OF THE INVENTION

According to a first aspect of the invention, a method is disclosed for diagnosing Alzheimer's Disease. The method comprises the steps of obtaining a non-neural tissue biopsy sample, contacting at least a portion of the sample with at least one antibody capable of identifying $\beta$-AP, a $\beta$-amyloid precursor protein fragment comprising $\beta$-AP, or a $\beta$-AP peptide fragment of about 8 or more amino acids, and monitoring the extent of the reaction between the sample and the antibody.

According to another aspect of the invention, a kit is disclosed for diagnosing Alzheimer's Disease, comprising one or more antibodies as noted above, and means for detecting the extent and specificity of the reaction of the antibody with a non-neural tissue sample.

These and other aspects of the invention and advantages attendant thereto will best be understood by a reading of the following definitions, detailed description, examples and appended claims.

DEFINITIONS

The term "amyloid" is defined herein as a proteinaceous filament of about 50–100 Angstrom diameter, having certain dye-binding properties (e.g., the binding of molecules of Congo red in a particular orderly array, such that when polarized light is passed through the amyloid, a green birefringent color is seen; and the binding of thioflavin S, which produces a green fluorescent signal when viewed in a microscope outfitted with epifluorescence), and accumulating progressively in the extracellular spaces of a tissue. An additional characteristic of amyloid is the presence of extensive $\beta$-pleated sheet protein conformation, as established by X-ray diffraction analysis. Amyloid is a generic term that refers to proteinaceous filaments as defined in this paragraph, regardless of the tissue in which they appear or the protein of which they are composed, and occurs in a wide variety of diseases. Notwithstanding the above definition, the instant invention is directed to the type of amyloid that is characteristic of Alzheimer's Disease and Down's Syndrome, the subunit protein of which is the β-amyloid protein defined below.

The term "β-amyloid precursor protein fragment comprising β-AP" as used herein is defined as a polypeptide that is a portion of a β-amyloid precursor protein which is larger than, but includes within it, the β-amyloid protein.

The term "β-amyloid precursor protein" as used herein is defined as a polypeptide that is produced by a gene localized in humans on the long arm of chromosome 21 and that includes within its carboxyl third the β-amyloid protein (β-AP). Examples of specific forms of the β-amyloid precursor protein which are currently known to exist in humans are the 695-amino acid polypeptide described by Kang et al., *Nature* 325: 733-736 (1987); the 751-amino acid polypeptide described by Ponte, et al., *Nature* 331: 525-527 (1988) and Tanzi et al., *Nature* 331: 528-530 (1988): and the 770-amino acid polypeptide described by Kitaguchi et al., *Nature* 331: 530-532 (1988).

The term "β-amyloid protein" (β-AP) as used herein is an approximately 4.2 kDa protein which, in the brains of AD and Down's syndrome patients, forms the subunit of the amyloid filaments comprising the center of the senile (amyloid) plaque and is deposited in small vessels and in amorphous, non-filamentous parenchymal (tissue) deposits. The β-AP can occur in a filamentous polymeric form (in this form it exhibits the Congo-red and thioflavin-S dye-binding characteristics of amyloid described in connection therewith). It can also occur in a nonfilamentous form ("preamyloid" or "amorphous" or "diffuse" deposits) in tissue, in which form no detectable birefringent staining by Congo red occurs. A portion of this protein in the form obtained from the meninges or meningeal blood vessels is described in U.S. Pat. No. 4,666,829 issued to Glenner et al. on May 19, 1987. β-AP when used in connection with this invention refers to an approximately 38-43 amino acid peptide that is substantially homologous to the form of the protein produced by the method described in the Glenner et al. patent, but which, according to the instant invention, is preferably extracted from the cerebral cortex of AD patients or, alternatively, from the skin (or other non-neural tissue) of AD subjects, although other sources of immunoreactive material including synthetic peptides having all or part (e.g., about 8 or more amino acid residues) of the sequence of β-AP can also be used in conjunction with this invention. In whatever form, β-AP is a hydrophobic 38-43 amino acid fragment of a large glycoprotein, referred to as the β-amyloid precursor protein, encoded by a gene on the long arm of human chromosome 21. It is further characterized by its relative mobility in SDS-polyacrylamide gel electrophoresis and its propensity to aggregate into polymeric filaments having the ultra-structural and tinctorial properties of amyloid. Its 43-amino acid sequence is:

| 1 | | | | | | | | | |
|---|---|---|---|---|---|---|---|---|---|
| Asp | Ala | Glu | Phe | Arg | His | Asp | Ser | Gly | Tyr |
| 11 | | | | | | | | | |
| Glu | Val | His | Gln | Lys | Leu | Val | Phe | | |
| 21 | | | | | | | | | |
| Ala | Glu | Asp | Val | Gly | Ser | Asn | Lys | Gly | Ala |
| 31 | | | | | | | | | |
| Ile | Gly | Leu | Met | Val | Gly | Val | | | |
| 41 | | | | | | | | | |
| Ile | Ala | Met | | | | | | | | or is substantially homologous thereto. It can be extracted from the cerebral cortex by the method described in Selkoe et al, *Journal of Neurochemistry* 46: 1820-1834, 1986, which is hereby fully incorporated into this disclosure by reference as though fully set forth herein (see also Example IA), or from the skin by the method set forth in Example IB below.

The term "β-AP peptide fragments of about 8 or more amino acids" as used herein means a fragment of β-AP (or a peptide substantially homologous thereto), capable of producing antibodies that will react with β-AP or a form thereof present in the skin or other non-neural tissues of AD subjects.

The term "brief fixation" as used herein in conjunction with the preparation of a biopsied skin sample or other non-neural tissue sample for AD diagnosis means treating the sample with an agent (termed herein as a "fixative") that stabilizes the molecules in the sample by cross-linking them or otherwise producing strong intramolecular and intermolecular bonds, this treatment occurring in a period of time that is long enough to produce structural stability and resistance to degradation of the proteins in the sample but not so long as to markedly alter the molecular form or conformation of β-AP-immunoreactive antigens in the sample. Typically, brief fixation in accordance with this invention will involve treatment with an aldehyde-containing fixative, such as 10% neutral buffered formalin, Bouin's solution (70% (vol/vol) saturated picric acid, 10% (vol/vol) formalin, 5% (vol/vol) glacial acetic acid) in water or PLP fixative (periodate-lysine-paraformaldehyde in relative concentrations (weight/vol) of 0.2%: 1.4%: 2% in water). Treatment time will preferably be from about 15 to about 60 minutes, although these times can vary from as little as about 10 minutes to as long as about 3 hours depending on the nature of the fixative. However, conventional fixation for prolonged periods (e.g., for weeks to months) can also be carried out.

The term "intestine" includes small intestine, large intestine (colon), and rectal tissue.

The term "skin biopsy sample" is defined herein for the purpose of the appended claims as including either or both of cutaneous and subcutaneous tissues.

DETAILED DESCRIPTION OF THE PREFERRED EMBODIMENTS

The subject invention results from the unexpected and entirely novel detection of β-AP deposits in tissues of non-neural organs in AD patients, including skin, subcutaneous connective tissue, and intestine. This discovery provides the first demonstration that the β-amyloid protein, which is invariably and progressively deposited in the brain in AD, is also present in non-neural tissues, particularly the skin and intestine. Accordingly, the invention is generally directed to a non-neural tissue sample and detecting the presence and quantity of β-AP (or a β-amyloid precursor protein fragment comprising β-AP) therein. The detection and quantitative measurement of β-AP in such tissue in accordance with this invention is useful in confirming a clinical diagnosis of AD in demented patients and in following the course of the illness. The invention can be applied, for example, to monitor the disease during a period of treatment with agents that stabilize, decrease or prevent the deposition of β-AP into tissues, including the brain.

According to the present invention, monoclonal or polyclonal antibodies produced to various forms of β-amyloid protein (or a β-amyloid precursor protein fragment comprising β-AP) can be used in an immunoassay on biopsied samples of skin, intestine, or other non-neural tissue to diagnose patients with Alzheimer's Disease (AD). A preferred embodiment involves testing such samples with antibodies produced by using the β-AP extracted from AD cerebral cortex as immunogen. The extraction can be carried out according to (or in a manner similar to) the method of Selkoe et al., *Journal of Neurochemistry* 46: 1820–1834 (1986) and of Selkoe and Abraham, *Methods in Enzymology* 137: 37–44 (1986), which articles are hereby fully incorporated by reference herein. The method of carrying out the preferred extraction is taught in Example IA below. Alternatively, the antibodies used for detection of the β-AP can be produced by the immunization with β-AP antigen extracted from the skin (or other non-neural tissue) of Alzheimer Disease victims, as described in Example IB. β-AP extracted from AD meningeal blood vessels or synthetic peptides having part or all of the sequence of β-AP can also be used as immunogens, although the resulting assays are generally less sensitive (see Table I).

The antibodies used in the diagnosis of the skin, intestine, or other non-neural tissue sample can be polyclonal or monoclonal, and can be made by methods now well-known in the art. For example, polyclonal antibodies made to the extract of Example IA or IB can be produced by immunizing an animal such as a rabbit and then purifying the antibodies as described in Example IC, while monoclonal antibodies to said extracts can be made, for example, according to the method of Kohler and Milstein (Nature (1975) 256:495) by immunizing an animal such as a mouse, extracting splenocytes from the spleen thereof, fusing them with mouse myeloma cells to make hybridomas, and screening and subcloning the hybridomas, all as described in Example ID.

It is interesting to note that non-neural β-AP deposits (like many so-called preamyloid deposits now known to occur in brain) are weakly or not reactive with the classical histochemical stains for amyloid, Congo red and thioflavin S; the skin, which demonstrates such deposits readily and is most easily sampled, has not been thought to be a site for β-amyloidosis in AD; and generally, antibodies to β-AP synthetic peptides are currently being used by AD investigators other than the inventor and his coworkers, but these detect non-neural deposits such as those in the skin much less sensitively than antisera to native cerebral β-AP such as those made by the inventor and his co-workers and shown in Table I. The instant discovery is particularly unexpected because of these and other factors. Antibodies produced from synthetic peptide immunogens which are generally used in the art for staining AD brain tissue include those listed in Table I as L and Y, which are similar to those described in U.S. Pat. No. 4,666,829 by Glenner and Wong. Moreover, as shown in Table I, the β-AP deposits are generally less detectable when using antibodies produced against immunogen extracted from the meninges of AD victims than when using antibodies produced against immunogen extracted from the cerebral cortex of AD victims. These observations suggest that the form of β-AP found in skin and other perivascular connective tissues resembles the native β-AP molecules in brain tissue more closely than it does synthetic β-AP peptides.

Interestingly, β-AP immunoreactivity found in the skin and intestine has certain properties that differ from β-AP found in the meninges or brain tissue. For example, the reactivity with antibodies to synthetic β-AP is generally destroyed by pretreatment with formic acid, in contrast to the enhancement of β-AP staining by synthetic peptide antibodies that this reagent generally produces in the brain deposits. Accordingly, in the preferred embodiment of the invention, skin and intestine samples should not be pretreated with formic acid, and should be preserved by brief fixation (e.g., from about 15 to about 120 minutes, preferably for about 30 minutes) in one of several possible fixatives, as described in full detail in Example III below.

In practicing the invention, a skin, intestine, or other non-neural tissue sample is removed from the patient by a biopsy procedure. Preferably, one or more punch biopsies are taken from an area of the skin with a low density of nerve endings and little sensory importance, such as the inside surface of the arm, to minimize discomfort, although other types of biopsy, such as an elliptically-shaped incisional biopsy, can be taken from any area of the skin. An intestinal biopsy can similarly be obtained by methods well-known in the art.

Samples of skin, intestine or other non-neural tissue obtained by a biopsy (punch biopsy or incisional biopsy) from patients suspected of having Alzheimer's Disease (or having another disorder characterized by β-AP deposition in brain, e.g., Down's syndrome or advanced aging) can be quick-frozen for subsequent β-AP extraction, solubilization and quantitative immunoassay. Alternatively, the non-neural tissue samples can be denatured in a fixative and then examined immunohistochemically.

For the purposes of extraction, solubilization and quantitation of the β-AP in skin, intestine, or other non-neural tissue, the samples should not be fixed but can be extracted in a buffer (e.g., those described in Example IB) or stored frozen until used.

For the purposes of immunohistochemical analysis, the preferred embodiment involves the fixation of the biopsied skin, intestine, or other non-neural tissue samples from the patients for brief periods of time. The purpose of such brief fixation is to avoid conformational alterations from prolonged fixation that could destroy the antigenic sites on the β-AP-containing molecules in the samples. For example, the samples can be fixed for 15–60 minutes in 10% neutral buffered formalin, following which the sample is removed to a physiological buffer (e.g., phosphate buffered normal saline, pH 7.6, with 0.02% sodium azide) and stored at 4° C. Alternatively, a longer period of fixation can be used, but in the preferred embodiments of this invention, brief fixation (i.e., fixation for generally less than three hours) is called for. Other fixatives can be used including a picric acid-containing fixative (e.g., Bouin's method) or the PLP fixative (periodate-lysine-paraformaldehyde).

After this treatment, the fixed sample can be further prepared for immunohistologic staining. For example, the sample can be embedded in a medium such as paraffin and sectioned in a microtome, and typically, 5-15 μm-thick sections can be mounted on glass microscope slides for immunocytochemistry. Alternatively, a microtome in a cryostat can be used to prepare frozen sections from either a fresh-frozen or a fixed-frozen sample of skin, intestine, or other non-neural tissue. The inclusion of some subcutaneous tissue in the skin sample is often useful diagnostically, since perivascular β-AP deposits can be seen to advantage in this region.

The skin (or other non-neural tissue) samples, whether mounted on slides or used free-floating, are then contacted (i.e., reacted) with an antiserum or monoclonal antibody, such as those prepared as described herein and set forth in Table I. The primary antibody, or a control aliquot following absorption of the primary antibody with a form of the β-AP immunogen, can then be placed on the sample and incubated for about 2 to about 4 hours, or overnight. Thereafter, the samples are washed and incubated with a secondary antibody reactive against the first, e.g., goat anti-rabbit IgG antibody or goat anti-mouse IgG or IgM antibody. The secondary antibody can be labelled. For example, it can be coupled directly to an enzyme marker such as peroxidase-antiperoxidase or can be coupled with biotin followed by reaction with an avidin-biotin complex coupled with peroxidase. Such a reaction product can be detected colorimetrically by incubation with 3,3'-diaminobenzidine (DAB). The stained sample is viewed through a light microscope.

Alternative methods for analysis of immunohistochemical sections include using an alkaline phosphatase-coupled secondary antibody; or using a fluorochrome-coupled second antibody (e.g., fluorescein), in which the reaction of the primary antibody with the fixed skin, intestine, (or other non-neural tissue) section is assessed using a light microscope outfitted with epifluorescence.

In the preferred embodiment, several β-AP antibodies (or antibodies to amyloid precursor protein fragments comprising β-AP or β-AP peptide fragments of 8 or more amino acids) produced as described in the following examples (and as further exemplified in Table I) can be used as primary antibodies to detect β-AP deposits in AD skin, intestine, or other non-neural tissue samples. Two types of controls can be provided by comparing the primary antibody-stained samples to: (1) like samples from the AD patient reacted with the immunogen-absorbed primary antibody or with normal rabbit serum, and (2) samples of normal tissue (free of β-AP) stained with the primary (i.e., anti-β-AP) antibody. In the preferred embodiments, controls are carried out to determine whether the suspected β-AP deposit that has been identified by a primary (i.e., anti-β-AP) antibody: (1) will produce a positive assay signal following absorption of the primary antibody with a form of β-AP, or (2) will be recognized by an irrelevant antiserum, an irrelevant monoclonal antibody or an irrelevant preimmune serum. The completeness of the absorption of the primary β-AP antibody by a β-AP antigen can be confirmed by reacting aliquots of both the unabsorbed and absorbed antibody with sections of AD brain tissue and demonstrating that known β-AP-containing lesions (e.g., senile plaques and amyloidotic blood vessels) in the brain are no longer stained by the absorbed antibody.

Once the deposition of β-AP in a skin, intestine, or other non-neural tissue sample is detected, the stained sample should be compared to standard immunohistochemical sections (both negative and positive controls), preferably provided with the kit of the present invention, in the case of the fixed samples; or to a standard antigen curve in the case of a quantitative immunoassay, or otherwise evaluated to determine whether the sample has tested positive for AD. An example of a quantitative competitive immunoassay is described in Example VII.

In an immunohistochemical analysis, the amount of β-AP immunoreactive deposits in the skin, intestine, or other non-neural tissue can be assessed semi-quantitatively (e.g., 0=absent; 1=weak staining; 2=moderate staining; and 3=strong staining) by the microscopist using a relative scale based on experience or simultaneously-assessed standards of known AD patients having β-AP skin (or other non-neural tissue) deposits. Alternatively, the approximate cross-sectional area of microscopic sections that contain β-AP immunoreactive material can be determined through the microscope using an ocular graticule (or other quantitative microscopy device) and compared to a standard range of the areas of such β-AP deposits previously determined in a series of AD versus like, age-matched, non-AD samples.

In addition to the use of immunohistochemistry as described above, another preferred embodiment involves the extraction of β-AP (and/or β-amyloid precursor protein fragments comprising β-AP) from fresh or fresh-frozen biopsied skin, intestine, or other non-neural tissue samples obtained from putative AD patients and from age-matched controls. The extraction of β-AP (or β-AP-containing molecules) and its solubilization can be carried out as described in Example IB. A β-AP antibody such as those described in the Examples or exemplified in Table I can be reacted in a diagnostic immunoassay using standard methods (see for example, Campbell, et al., *Methods of Immunology* (1964)). A radioimmunoassay (RIA) or enzyme-linked immunosorbent assay (ELISA) can be employed for immunodetection of an extracted, preferably solubilized, form of β-AP. A variety of labels can be used, such as radioisotopes that include $^{125}I$, $^{14}C$, $^{3}H$, enzymes, fluorophores or chemiluminescent molecules. The amount of β-AP-immunoreactive molecules extracted from the biopsied samples can be compared to a standard curve, whether using a competitive or non-competitive assay.

Table I below sets forth six distinct, well-characterized antisera to native or synthetic β-AP which detect β-amyloid protein tissue deposits: namely, antisera A, C, F, Y, Ph and L. Antisera A and C were produced against AD cortical β-AP immunogen, as described in Selkoe et al., *J. Neurochem.* 46: 1820-1834 (1986) and Selkoe et al., *Science* 235: 873-877 (1987), while antiserum L was produced against synthetic β-AP immunogen, as described in the latter. Antisera F and Ph were produced against AD meningovascular β-AP immunogen, as described in Joachim et al., *Brain Research* 474: 100-111 (1987). Antiserum Y was prepared as described in Example II below.

In addition, Table I sets forth six irrelevant antisera for comparison, namely, antibodies P, DJ, G, T, AA and CB7. Antiserum P is described in Ihara, Abraham, Selkoe, *Nature* 304, 727-730 (1983). Antiserum DJ is described in Selkoe, Bell, Podlisny, Price, Cork, *Science* 235, 873-877 (1987). Antiserum G is described in Dahl, *Brain Res.* 57, 343-360 (1973). Antiserum T was obtained from Calbiochem. Antiserum AA is described in Shirahama, Cohen & Skinner, in *Advances in Immunohistochemistry*, 277-302, (1984). Monoclonal antibody CB7 is described in Ju, Skinner, Shirahama & Cohen, *Fed. Proc.* 46, 1326 (1987). The references cited in this paragraph are hereby fully incorporated into this disclosure by reference.

To confirm the specificity of antibodies to β-AP, they were absorbed with highly purified β-AP. While the β-AP-specific antibodies detected the tissue deposits before this absorption, they did not do so afterwards, confirming that they were in fact detecting β-AP as deposited in the skin or intestine. Similarly, the antibodies stained β-amyloid deposits in the brain before, but not after, the antibodies were absorbed with β-AP specific antigen. Antigen-absorbed and "control-absorbed" aliquots (both in 150 mM NaCl, 50 mM Tris, pH 7.6) were reacted simultaneously with AD brain sections, AD skin or intestine sections and dot blots of the β-AP-containing antigen. In the case of antiserum A, for example, a partially purified fraction of detergent-extracted senile plaque cores from AD cerebral cortex (as described in Example IA, below) was used as the absorbent; a "control absorption" employed a fraction prepared identically from normal aged human cerebral cortex which contained the contaminating particles of core fractions (e.g., lipofuscin granules, collagen, and microvessel fragments). In each such experiment, the AD plaque core absorption markedly diminished or abolished the staining of plaque and vascular amyloid in AD brain, the dermal and subdermal amorphous β-AP deposits, and the β-AP-containing antigen on dot blots. The control absorptions produced no change in these immunoreactions. Similar results were obtained with each of the other β-AP antisera listed in Table I after absorption with relevant antigen. Preimmune sera, secondary antibody alone and various hyperimmune sera (see Table I) to purified paired helical filaments (PHF), tau protein, human glial fibrillary acidic protein, and human transthyretin (prealbumin), all failed to label specifically the skin β-AP deposits The six β-amyloid antisera varied greatly in the sensitivity of their detection and precise staining patterns on non-neural β-AP deposits. Antiserum A, produced to the native 4.2 kDa β-AP purified by HPLC from amyloid filaments extracted from AD cerebral cortex, was the most sensitive detector. Antisera to HPLC-purified meningovascular β-AP (F and Ph in Table I) and to the synthetic β-1-38 peptide (Y in Table I) were considerably weaker, although the intensity of labeling at a standard dilution of any one particular antibody varied from case to case and even among the β-AP deposits found within one skin section of a particular AD case.

The sensitivity ratings set forth in Table I are based upon the relative detection of β-AP in adjacent skin sections from the same AD patient. The ratings are based upon a peroxidase/ diamino-benzidine (DAB) immunodetection system and are intended as an example of the variability among different β-AP antibodies in detecting skin β-AP deposits. A rating of high means moderately intense or intense brown (DAB-positive) immunoreaction product; a rating of moderate means medium or medium-low intensity of brown reaction product; and a rating of minimal means barely detectable brown reaction product, under the specific immunohistochemical conditions used. A high intensity rating for a given antibody is preferred for ease of interpretation of results.

Table II summarizes the results of an examination of skin, subcutaneous tissue or colon from 41 human subjects: 11 with AD, 26 without AD and 4 with Down's Syndrome. All but 4 had been autopsied, establishing precise neuropathological diagnoses. Eight of the 11 AD cases showed definite β-AP-reactive non-neural deposits and two showed slight, equivocal reactivity. In contrast, only 3 of 26 non-AD subjects showed definite non-neural βAP reactivity; all of these were ≧77 years old. Of 4 Down's syndrome skin samples, 2 were positive and 2 were equivocal. In addition to autopsy-proven cases, fresh punch biopsies of forearm skin were examined from one AD and one normal subject: the former showed specific βAP-staining, whereas the latter did not.

βAP-immunoreactive deposits were located in the dermis in a patchy distribution beneath the epidermal/dermal junction, sometimes near small blood vessels or glandular elements. The stained material appeared to be localized extracellularly among connective tissue fibers in the reticular dermis. Some deposits were found circumferentially around small vessels, particularly arterioles. Most vessels and other skin structures (sweat and sebaceous glands; hair follicles; hair shafts; smooth muscle; epidermis; keratin) were unstained, attesting further to the specificity of the reaction. In subcutaneous tissue and the submucosal tissue of the colon, β-AP-reactivity was found around microvessels and in perivascular connective tissue, apparently extracellular. Deposits of β-AP were most easily visualized in the intestine (both small and large), because they often occurred in a distinct vascular locus resembling that found in the brain and meninges. Almost all of the dermal deposits observed had an amorphous, non-fibrillar appearance, resembling somewhat the diffuse β-AP deposits abundantly present in AD brains and the brains of some patients with hereditary cerebrovascular β-amyloidosis of Dutch type. The non-neural deposits lost their reactivity with antibodies to synthetic β-AP (Y in Table I) when sections were pretreated with formic acid, a reagent that can enhance the staining of some brain β-AP deposits. The deposits in skin were not detected by Congo red or thioflavin S.

These results provide the first demonstration that the β-amyloid protein, which is invariably and progressively deposited in the brain in AD, is also deposited in extracerebral tissues. Tests on four specific antibodies (A,C,F and Y, Table I) to native or synthetic β-AP showed detection of the tissue deposits before but not after βAP antigen absorption; staining of β-amyloid in brain was simultaneously abolished. Antisera to proteins other than β-AP tested to date do not label the non-neural deposits.

Of course, it should be understood that the foregoing detailed description of preferred embodiments and the following Examples are merely illustrative and not limiting. Many variations will be apparent to one of ordinary skill in the art, and accordingly, the invention is intended to be limited only in accordance with the claims and all legal equivalents thereto.

TABLE I

| SUMMARY OF ANTIBODIES | | |
| --- | --- | --- |
| Antiserum | Immunogen | Assay Sensitivity |
| A | ~4 kD βAP purified by HPLC from AD cortex | high |
| C | ~4 kD βAP purified by HPLC from AD cortex | moderate |
| F | ~4 kD βAP purified by HPLC from AD meninges | moderate |
| Y | synthetic βAP$_{1\text{-}38}$ peptide | moderate |

TABLE I-continued

SUMMARY OF ANTIBODIES

| Antiserum | Immunogen | Assay Sensitivity |
|---|---|---|
| Ph | ~4 kD βAP purified by HPLC from AD meninges | minimal |
| L | synthetic βAP$_{1-28}$ peptide | minimal |
| *P | isolated paired helical filaments | negative |
| DJ | heat-stable MAPs (including tau) from bovine brain | negative |
| *G | glial fibrillary acidic protein | negative |
| *T | human transthyretin | negative |
| *AA | isolated AA amyloid fibrils | negative |
| Monoclonal Antibody | | |
| *CB7 | isolated AA amyloid fibrils | negative |

*Series of irrelevant hyperimmune sera (see Examples II and III), presented for comparison only.

Antisera A and C are described in Selkoe, Abraham, Podlisny, Duffy, J. Neurochem. 46, 1820–1834 (1986) and Selkoe, Bell, Podlisny, Price, Cork, Science 235, 873–877 (1987).
Antiserum L is described in and Selkoe, Bell, Podlisny, Price, Cork, Science 235, 873–877 (1987).
Antiserum F and Ph are described in Joachim, Duffy, Morris, Selkoe, Brain Res. 474, 100–111 (1988).
Antiserum Y is described in Example I.C. herein.
Antiserum P is described in Ihara, Abraham, Selkoe, Nature 304, 727–730 (1983).
Antiserum DJ is described in Selkoe, Bell, Podlisny, Price, Cork, Science 235, 873–877 (1987).
Antiserum G is described in Dahl, Brain Res. 57, 343–360 (1973). Antiserum T was obtained from Calbiochem.
Antiserum AA is described in Shirahama, Cohen & Skinner, in Advances in immunohistochemistry, 277–302, (1984).
Monoclonal antibody CB7 is described in Ju, Skinner, Shirahama & Cohen, Fed. Proc. 46, 1326 (1987).

Table II, set forth below, demonstrates the method of the present invention for the diagnosis of AD. Demonstrable immunoreactivity is generally diagnostic of AD, and is indicated by the +values shown in the Table.

TABLE II

βAP IMMUNOREACTIVITY IN NON-NEURAL TISSUE SAMPLES FROM 41 HUMAN SUBJECTS

| Subject # | Age/Sex | Neurological Diagnosis | Neuropathology | βAP Immunoreactivity Skin | βAP Immunoreactivity Intestine |
|---|---|---|---|---|---|
| ALZHEIMER'S DISEASE | | | | | |
| *Skin:* | | | | | |
| A88-46 | 89 F | AD (>5)[1], remote CVA | AD, sl. AA; remote CVA | + | |
| X1330 | 85 M | AD (6) | [living patient] | + | |
| A88-77 | 84 M | AD (14) | AD, mod. AA | + | |
| A88-218 | 82 M | AD (2) | AD, sl. AA, acute CVA | + | |
| A85-196 | 78 M | AD (7) | AD, marked AA | + | |
| A86-55 | 77 F | AD/PD (1) | AD/PD[2], mod. AA | + | |
| A87-237 | 76 F | AD (7) | AD, mod. AA | − | |
| A87-48 | 74 F | AD (4) | AD, slight AA | ± | |
| A89-10 | 71 M | AD (5) | AD, mod. AA | + | |
| A89-14 | 62 F | AD (8) | AD, mod. AA | ± | |
| *Intestine:* | | | | | |
| A88-46 | 89 F | AD (>5), remote CVA | AD, sl. AA; remote CVA | | ± |
| A88-159 | 87 F | AD (>5) | AD, marked AA | | ± |
| AGED DISEASED | | | | | |
| *Skin:* | | | | | |
| A87-144 | 83 F | PD, dementia (5) | No PD, sl. sp, no AA | − | |
| A88-233 | 82 F | PD (8), dementia (1) | Nigral/pallidal degen., no sp, slight AA | − | |
| A88-52 | 81 M | Remote poliomyelitis | Remote polio, no sp, no AA | + | |
| A88-130 | 79 M | Remote CVA | Remote CVA, sl. sp, no AA | − | |
| A89-40 | 78 M | Mental retardation | Remote contusion no sp, no AA | + | |
| A88-125 | 77 F | Remote CVA | Remote CVA, mod sp; sl. AA | − | |
| *Intestine:* | | | | | |
| A88-125 | 77 F | Remote CVA | Remote CVA, mod. sp, sl. AA | | + |
| A88-194 | 62 F | Carcinoma | Metastic carcinoma no sp, no AA | | − |
| AGED NORMAL | | | | | |
| *Skin:* | | | | | |
| A87-45 | 80 M | Normal | Rare sp, slight AA | ± | |
| A87-147 | 76 M | Normal | No sp, mod. AA | − | |
| A87-302 | 72 F | Normal | No sp, no AA | − | |
| A88-347 | 72 M | Normal | No sp, slight AA | ± | |
| X1362 | 64 M | Normal | [living patient] | − | |
| NON-AGED NORMAL | | | | | |
| *Skin:* | | | | | |
| A87-268 | 61 F | Normal | Normal | − | |

TABLE II-continued

βAP IMMUNOREACTIVITY IN NON-NEURAL TISSUE SAMPLES FROM 41 HUMAN SUBJECTS

| Subject # | Age/Sex | Neurological Diagnosis | Neuropathology | βAP Immunoreactivity Skin | Intestine |
|---|---|---|---|---|---|
| A89-3 | 60 M | Brain tumor | Glioblastoma | − | |
| A88-376 | 56 F | Normal | Normal | − | |
| A88-259 | 55 F | Normal | ND | − | |
| A88-258 | 49 M | Normal | Normal | − | |
| A88-358 | 45 M | Normal | Normal | − | |
| A88-367 | 45 F | Normal | Normal | − | |
| A83-256 | 42 M | Spinal cord trauma | Traumatic myelopathy | − | |
| A88-280 | 35 M | Brain tumor | Glioblastoma | − | |
| A88-368 | 32 M | Normal | Normal | − | |
| A88-300 | 30 M | Normal | ND | − | |
| A88-159 | Fetus | Prematurity | Germinal matrix hemorr. | − | |
| Intestine: | | | | | |
| A88-183 | 38 F | Normal | Normal | | − |
| A88-160 | 24 F | Normal | Normal | | − |
| DOWN'S SYNDROME | | | | | |
| Skin: | | | | | |
| A80-40 | 44 F | Down's syndrome | Mod. sp, sl. AA | + | |
| A85-140 | 38 M | Down's syndrome | Mod. sp, no AA | ± | |
| A86-98 | 36 F | Down's syndrome | Mod. sp, slight AA | ± | |
| A77-61 | 25 M | Down's syndrome | Mod. sp, no AA | + | |

[1]Approximate duration (in years) of disease.
[2]Typical neuropathological findings of both AD and PD.
AD, Alzheimer's disease; PD, Parkinson's disease; AA, amyloid angiopathy; CVA, cerebrovascular accident; sp, neocortical senile plaques; mod., moderate; sl, slight; +, define, specific staining; −, no staining; ±, slight or equivocal staining. ND, not determined.

EXAMPLES

Example I

Immunogen and Antibody Production

A. Extraction of β-Amyloid Protein from the Cerebral Cortex

Human brains of patients who died with Alzheimer's Disease were removed at autopsy and frozen at −70° C. For extraction of β-AP from brain, only brain tissue markedly enriched in β-AP deposits (i.e., in both plaques and microvascular β-AP) was used. A rapid, quantitative light microscopic assay that relies on the insolubility of neurofibrillary tangles and senile plaque amyloid cores in sodium dodecylsulfate (SDS) was developed and used to identify the β-AP enriched brain tissue, as follows. Frozen cerebral cortex (50–100 mg) was dissected from 10 representative brain areas, homogenized briefly in 2% SDS buffer (2% SDS/0.1 M β-mercaptoethanol (β-ME)/50 mM Tris-HCl, pH 7.6), heated to 100° C. for 5 min., and pelleted at 10,000 g for 5 min. The pellets were re-suspended in 50 μl of 2% SDS buffer, placed on albumin-coated slides, and stained with 1% Congo red in water. Using a polarizing microscope, the number of birefringent cores and/or tangles can be counted or a semiquantitative estimate (e.g., 0-4+, where 0 means no cores and 4+means a large number of cores) can be made. During amyloid core purification, a modification of this assay was used in which 5 μl of 0.2% Congo red were mixed with 5 μl of the fraction and placed in a hemocytometer to count precisely the yield and purity of the cores at each step.

Frozen cerebral cortex (20–100 g) was selected from areas found to be markedly enriched in β-AP-containing amyloid deposits by the assay just described. The tissue was dissected free of visible blood vessels and meningeal fragments, minced with a scalpel and incubated for 2 hours in five volumes of 2% SDS buffer (see FIG. 1 of Selkoe et al., J. Neurochem. 46:1820–1834 (1986)). The suspension was homogenized (Dounce, pestle B, 20 strokes), heated at 100° C. for 10 min., and sieved through 100 μm nylon mesh (Nitex). The filtrate was centrifuged at 300 g for 30 min. The supernatant (containing abundant neurofibrillary tangles among other contaminants) was frozen for a separate purification of neurofibrillary tangles. The pellet was washed and pelleted (300 g, 10 min.) three times in 0.1% SDS solution (0.1% SDS/150 mM NaCl/0.2% NaN$_3$). This pellet was homogenized; sieved through 35 μm Nitex; loaded on a gradient composed of layers of 1.2 M, 1.4 M, 1.6 M, and 1.8 M sucrose in 1% SDS/50 mM Tris; and centrifuged in an SW 28 Beckman rotor at 72,000 g for 60 min. Each interface was collected, diluted five-fold in 0.1% SDS solution, and pelleted at 300 g for 30 min. A small aliquot from each pellet was assayed as above to assess core enrichment. In most AD cases, the 1.6/1.8 and 1.4/1.6 M sucrose interfaces showed the greatest enrichment. Pellets from these layers were stored at 4° C. until further use. The 1.4/1.6 M and the 1.6/1.8 M sucrose gradient interfaces can be used without further purification as immunogens to raise polyclonal and monoclonal antibodies, following their extensive sonication and their combination with complete or incomplete Freund's adjuvant, or can be used as immunogens following their solubilization in concentrated formic acid followed by lyophilization, resuspension in a buffer and further purification of the β-AP by HPLC. Alternatively, the following further purification of the immunogen can be carried out.

The post-gradient core fractions were Dounce-homogenized (pestle B, 10–20 strokes) and sieved through 35 μm Nitex just prior to loading on a Becton Dickinson FACS 440 cell sorter. Each fraction was analyzed on the FACS as to forward angle light-scattering (particle size) and fluorescence intensity. Based on the size range of isolated cores, the instrument was programmed to separate particles of ∼5–30 μm diameter from smaller and larger particles and simultaneously to separate the 5–30 μm particles into two subpopulations displaying bright or dull autofluorescence. The samples were sorted in 0.1% SDS solution at a flow rate of 2,000–5,000 particles per second using an 80 μm nozzle and an argon laser with an excitation maximum at 488 nm, and emission picked up by a 580 nm dichroic filter followed by a 580 nm long pass filter.

Following the first FACS sort, the fractions were assayed for cores, and the dull autofluorescent fraction, containing the large majority of sorted cores, was fluorescently immunolabeled. For this purpose, any of the β-AP antibodies listed in Table I or a similar antibody can be used. Here, for example, partially purified cores (prepared as above through the sucrose gradient step) were used as an immunogen in a rat or a rabbit to raise crude amyloid core antibodies. After an initial injection (~200 μg protein in complete Freund's adjuvant) and four boosts (50–100 μg each in incomplete Freund's adjuvant), the rat serum labeled the SDS-isolated cores at ~1:2,000 dilution. The serum was absorbed overnight at 1:1,000 dilution with an homogenate of the SDS-insoluble fraction of normal aged human cerebellum. The post-first-FACS core fraction was incubated (4° C., 18 hr.) with the absorbed antiserum (or with a β-AP antiserum from Table I) in TBS (150 mM NaCl, 50 mM Tris, pH 7.6). The labeled cores were pelleted, washed twice in TBS, labeled with rhodamine-conjugated goat anti-rabbit IgG antibodies (1:20, 2 hr.), and washed twice. The cores were examined by fluorescence microscopy, briefly homogenized, and sorted in the FACS for a second time. Analysis usually indicated two discrete populations of fluorescent, 5–30 μm particles (or a single peak with a more brightly fluorescent shoulder), and these were separated. The brighter fraction contained highly purified cores, which were heated (100° C., 5 min.) in 1% SDS to remove IgG, washed three or four times (300 g, 10 min.), and stored at 4° C. Particle purity was determined by light and electron microscopy.

An alternative method of preparing isolated amyloid filaments from AD cerebral cortex can be used. This is as described by Selkoe and Abraham in *Methods in Enzymology* 134: 37–44 (1986). The method yields mixed fractions of neuronal-derived paired helical filaments and extraneuronal amyloid filaments. Since the latter elements can be quite enriched in the fractions produced by this method, it can be used to advantage to obtain β-AP for use as immunogen in the practice of this invention. Indeed, HPLC-purified β-AP extracted from fractions prepared by this method were used as the immunogen to produce antiserum A (Table I), which sensitively detects deposits of β-AP in AD skin and other non-neural tissues. Cerebral cortex (20–100 g) containing abundant vascular and plaque amyloid deposits is dissected from frozen coronal brain sections based on the results of the semiquantitative Congo red assay described previously. Meninges, white matter, and visible blood vessels are carefully removed and the cortex is finely minced with a scalpel blade. The tissue is incubated for 2 hours in 5 vol. of 2% SDS buffer (2% SDS/0.1 M β-ME/50 mM Tris-HCL, pH 7.6) and homogenized in a Dounce glass homogenizer using 10–20 strokes with a loose-fitting (B) pestle. The homogenate is heated to 100° C. for 5 min. and sieved once through 110 μm nylon mesh (Nitex). The filtrate is spun at 300 g for 30 min. The pellet, which contains the vast majority of senile plaque amyloid cores in the homogenate as well as large NFT (~15–20 μm diameter), some blood vessel fragments, some lipofuscin granules, and other larger contaminants, is stored at −70° C. for a separate purification of amyloid cores. The supernatant is aspirated with a Pasteur pipet and centrifuged at 100,000 g for 30 min. in a fixed-angle rotor. The pellets are resuspended in 1% SDS buffer (1% SDS/0.1 M β-ME/50 mM Tris-HCl, pH 7.6) at a ratio of approximately 1 ml/1.5–2.0 g starting cortex and re-homogenized with a tight-fitting (A) Dounce pestle.

The resulting suspension is made 0.4 M in sucrose and layered on top of a discontinuous sucrose gradient in 38 ml Beckman ultraclear ultracentrifuge tubes: 5 ml of 2.0 M sucrose, 8 ml of 1.4 M sucrose, 8 ml of 1.2 M sucrose, and 7 ml of 1.0 M sucrose (all in 1% SDS/50 mM Tris-HCl buffer). The gradients are immediately spun at 145,000 $g_{max}$ (27,000 rpm) for 240 min. in an SW28 rotor. Relatively well-defined bands are observed as follows: brown bands at the top of the 1.0 M sucrose layer and at the 1.0/1.2 M interface, hazy white bands at the 1.2/1.4 and 1.4/2.0 M interfaces, and a very small pellet. Each fraction is collected with a Pasteur pipet, diluted at least 5 times with 1% SDS buffer, and pelleted at 100,000 g for 60 min. in a fixed angle rotor.

To purify such sucrose gradient fractions further, the pellets are re-suspended in 1 ml of 1% SDS buffer, sonicated for 30 sec. (Kontes sonicator; power setting 8; tune 4), and spun at 14,000 g for 30 min. (Beckman Type 40 rotor). The pellet, containing larger aggregates of lipofuscin plus PHF fragments, is discarded; the supernatant is centrifuged at 176,000 g for 60 min. Electron microscopy of this final pellet reveals relatively homogeneous fields of randomly oriented small fragments of PHF and amyloid filaments. Small fragments of lipofuscin and fine, dense granules remain as contaminants, but lipofuscin contamination is less than in the unsonicated sucrose gradient fraction. The sonicated PHF and amyloid fiber fragments retain their green birefringence when stained with Congo red after high-speed pelleting.

B. Extraction of β-Amyloid Protein from the Skin or Other Non-Neural Tissue

The immunogen used to produce the antibodies to β-AP that recognize the skin deposits in AD patients can also be prepared from the skin itself. Frozen or fixed sections of skin samples are first examined immunohistochemically to determine the extent of β-AP deposition using antibodies such as those in Table I. Fresh or fresh-frozen samples of β-AP-rich skin collected at autopsy from patients who died with pathologically confirmed AD can be extensively minced and then homogenized in a physiologic buffer (e.g., phosphate buffered normal saline, pH 7.4). Following differential centrifugation, the supernatant and the insoluble material of skin are separated. The supernatant is assayed for the presence of β-AP using, for example, an enzyme linked immunosorbent assay (ELISA) or radioimmunoassay (RIA) incorporating antibodies such as those in Table I. If the supernatant is found to contain β-AP immunoreactivity, it can be further fractionated by both conventional chromatographic procedures and affinity binding methods to obtain an enriched fraction of the β-AP molecule from skin. If the insoluble pellet of the first centrifugation demonstrates β-AP reactivity by the immunoassay, the pellet can be differentially extracted in certain detergents and/or salts (for example, 1–2% triton X-100, 1–2% sodium-dodecylsulfate, 6 M guanidine hydrochloride, or 6 M urea). Each extract of the insoluble pellet is then tested for β-AP immunoreactivity by immunoassay. Once solubilized β-AP is detected in a particular extract, this extract can be further purified chromatographically (e.g., by HPLC) and/or by affinity binding methods. Fractions enriched in β-AP derived in this way can be injected into rabbits for production of polyclonal antibodies or into mice for production of monoclonal antibodies by hybridoma techniques.

C. Production of Polyclonal Antibodies

To prepare the β-AP immunogen for production of the preferred polyclonal antibodies for this invention, the partially purified or the purified amyloid plaque cores or the paired helical filament/amyloid filament-enriched fractions, each prepared from AD cerebrum as described above, were then treated with 6.8 M guanidine SCN followed by dialysis and lyophilization or with 88% formic acid followed by lyophilization. The lyophilates were dissolved in 1% SDS, incubated at 37° C. for 30 min. and centrifuged at 10,000 g. The supernatant was applied to a Spectra-Physics 8700 HPLC system consisting of two TSK G3000 SW columns (Bio-Rad) connected in series and equilibrated with 0.1% SDS/150 mM Na phosphate, pH 6.8, and run at 0.5 ml/min. Proteins were detected at 220 nm and peaks were collected with a Gilford 201 fraction collector.

Both types of β-amyloid fiber preparations (purified amyloid cores or isolated PHF/amyloid filament preparations) yield similar HPLC chromatograms usually showing two major protein peaks having approximate molecular weights of 3–7 kDa and 11–15 kDa (see FIG. 5 of Selkoe et al., *Journal of Neurochemistry* 46: 1820–1834 (1986), incorporated fully by reference herein). Either or both HPLC fractions (or other β-AP containing chromatographic fractions) can be used as immunogens in either rabbits (to produce polyclonal antibodies) or in mice (to produce monoclonal antibodies by conventional hybridoma techniques). For example, 250 μg of protein were used, from the 11–15 kDa HPLC fraction of either formic acid-solubilized amyloid cores or formic acid solubilized PHF/amyloid filament fractions, to immunize rabbits. The antisera that resulted are represented by antisera A and C in Table I.

An alternate method of preparing the immunogen for antibody production involves the production of synthetic peptides having partial or complete sequences of the β-AP, their coupling to various carriers (e.g., keyhole limpet hemocyanin, rabbit serum albumin, edestin, etc.) and then immunization into rabbits by conventional procedures in complete or incomplete Freund's adjuvant. Antisera that resulted from this procedure are exemplified by Antisera Y and L in Table I.

D. Production of Monoclonal Antibodies

The injection schedule used to generate monoclonal antibodies is as follows. Approximately 10 μg/ml of the antigen is emulsified in complete Freunds Adjuvant and injected intraperitoneally. On day 15 and day 28 post initial injection, approximately 5 μg of antigen is emulsified in incomplete Freunds Adjuvant and injected intraperitoneally. The mouse is rested for 21 days and then injected intraperitoneally with approximately 10 μg of antigen. The mouse spleen is fused three days later.

The fusion protocol uses the following materials: Dulbecco's Modified Eagle's Medium (DMEM) with high glucose; Polyethylene Glycol 1500, screened for fusions, obtained from Boehringer Mannheim, West Germany; Fetal Bovine Serum (FBS), obtained from JR Scientific, Woodland, Calif.; 200 mM tissue culture grade Glutamine; $10^{-2}$M tissue culture grade hypoxanthine; 200 μg/ml of tissue culture grade Azaserine; 0.93 percent ammonium chloride; 3% Dextran (the high molecular weight fraction); IM tissue culture grade HEPES Buffer, pH 7.2; a 35 ml sterile petri dish; sterile forceps and dissecting scissors; fifteen sterile 96-well flat-bottom tissue culture plates with lids; a twelve channel pipet and sterile tips therefor; two sterile microscope slides with frosted ends; SP2/0 cells obtained from American Type Culture Collection (Rockville, Md.).

On the day of the fusion, two different media are prepared. The first is a growth medium containing 400 ml of DMEM, 100 ml of FBS, 5 ml of 200mM glutamine, 7.5 ml of IM HEPES buffer, pH 7.2, and 5 ml of $10^{-2}$M hypoxanthine. The other medium that is prepared is the selection media, comprising 75 ml of growth media to which is added 750 μl of 200 μg/ml azaserine.

The mouse is killed and then immersed in 70% ethanol for 10 seconds. The mouse is placed in a flow hood, and the spleen is aseptically removed, and placed in a 35mm petri dish containing 5 ml of growth media. The spleen is dissociated between the frosted ends of the slide. The spleen cell suspension is placed in a 15 ml sterile tube. The petri dish is rinsed with 10 ml of growth media and placed in the same 15 ml tube.

The SP2/0 cells are counted. (The density is generally greater than about 0.5 million cells per ml and less than about 0.9 million per ml.) The viability of the cells is generally greater than about 95% as estimated by trypan blue exclusion. Approximately fifty million cells are then placed into sterile 50 ml tubes. Both the spleen cells and the SP2/0 cells are then centrifuged in a clinical centrifuge for 10 minutes at 500×g.

The supernatant is removed from the spleen cells, and they are resuspended in 8 ml of ammonium chloride at about 4° C. This is allowed to incubate on ice for 5 minutes.

The SP2/0 cells are resuspended in 15 ml of plain DMEM. When the five minutes incubation of the spleen cells is complete, the suspended spleen cells are removed from debris pellet and added to the SP2/0 cells. DMEM is added to this cell mixture until the total volume is 25 ml. 25 ml of the 3% dextran is added to the spleen −SP2/0 cell mixture and this is incubated for 5 minutes. The cells are centrifuged at 500×g for 10 minutes.

The supernatant is removed from the pellet, and the pellet is then loosened by vortexing. 1 ml of the PEG 1500 is added. The tube is then vortexed and slowly rotated for one minute. This step is the actual fusion step.

25 ml of DMEM is added to the tube and this is incubated for one minute. After this incubation, 25 ml of growth media is added and incubated for one minute. The cells are centrifuged at 500×g.

The pellet is resuspended in 75 ml of selection media. A 12 channel pipet is used to place 50 μl into each well of the fifteen 96-well plates.

Two days after the fusion, each well is fed 50 μl of growth media. On day five post fusion, 50 μl are removed and the fusion is fed 100 μl of growth media. Visible hybrids are observed between day seven post-fusion and day ten post-fusion. At this time, the fusion is fed 100 μl of growth media. Screening generally begins around day ten. If hybrids are not ready to be screened on day ten, 150 μl of media are removed and 150 μl of fresh growth media are added thereto.

Viable hybridoma supernatants are screened for β-AP skin monoclonal antibodies by immunohistochemistry as described above.

EXAMPLE II

Observations in Pathologically Confirmed AD Victims

In an initial experiment, non-keratinized perianal skin (including cutaneous and subcutaneous tissue) was taken at autopsy from a 78-year-old man with a seven year history of clinically typical AD and severe AD brain lesions, including marked β-AP-positive amyloid angiopathy in cortical and meningeal arterioles. Reaction of formalin-fixed sections with an antiserum (antibody Y in Table I) raised to a synthetic peptide comprising residues 1–38 of β-AP (residues 597–634 of the β-AP precursor described by Kang et al., *Nature* 325:733–736 (1987)) showed specific, peptide-inhibitable labeling of amorphous material deposited multifocally in the connective tissue and periarteriolar spaces of the dermis. Adjacent sections from this block and skin samples from several other pathologically confirmed AD patients (Table II) were then examined with certain well-characterized antibodies to purified native β-AP (A,C, and/or F in Table I), synthetic β-AP peptide (Y in Table I) or unrelated proteins (Table I). The β-AP antibodies tested showed specific immunolabeling of amorphous proteinaceous deposits in the dermis and subcutaneous tissue, of AD patients (Table II). The sensitivity of detection differed considerably among the antisera. In seven of ten confirmed AD patients, clear β-AP immunoreactivity was observed in the skin. Two AD patients showed equivocal staining and, in one, staining was absent.

To determine the specificity of the immunoreactions, antigen-absorbed and "control-absorbed" aliquots of each β-AP antiserum tested were reacted simultaneously with AD brain, AD skin and dot blots of the antigen. In the case of antiserum A, for example, partially purified, SDS-extracted senile plaque cores were used as the absorbent; a control absorption employed a fraction prepared identically from normal cortex which contained the contaminating particles of core fractions (lipofuscin granules, collagen and microvessel fragments). In each such experiment, the plaque core absorption markedly diminished or abolished the staining of plaque and vascular amyloid in AD brain, the dermal and subdermal amorphous deposits, and the antigen on dot blots; these reactions were all carried out simultaneously with the same batch of absorbed antiserum. Control absorptions produced no change. Similar results were obtained with the other β-AP antisera. Preimmune sera, secondary antibody alone and hyperimmune sera to purified PHF (P), tau protein (DJ), glial fibrillary acid protein (G), transthyretin (prealbumin) (T) or amyloid AA protein (as well as a mouse monoclonal antibody to amyloid AA protein) all failed to label the skin deposits.

The β-AP-immunoreactive deposits detected in the dermis appeared in a patchy, multifocal distribution beneath the epidermal/dermal junction, sometimes near small blood vessels or glandular elements such as sweat and sebaceous glands. The stained material appeared to be localized extracellularly among connective tissue fibers in the reticular dermis. It was found amongst the normal collagen and elastin fibers of the dermis. Some deposits were found circumferentially around small blood vessels. Such deposits involved a minority of microvessels; most vessels and other skin structures (sweat and sebaceous glands; hair follicles; hair shafts; smooth muscle, epidermis) were entirely unstained, attesting further to the specificity of the immunoreaction. In subderma 1 tissues, amorphous β-AP-reactive material was occasionally found around microvessels, in connective tissues or around bundles of muscle fibers, apparently extracellular. Almost all of the deposits that were observed had an amorphous, non-fibrillar appearance resembling somewhat the diffuse, preamyloid deposits of β-AP present in AD brains, in aged normal human brains, and in the brains of some patients with hereditary cerebrovascular β-amyloidosis of Dutch type (Van Duinen et al, *Proc. Natl Acad Sci, USA* 84:5991–5994 (1987)). However, the deposits lost their reactivity with antibodies to synthetic β-AP (e.g., Y in Table I) if the sections were pretreated with formic acid, a reagent that generally enhances the immunostaining of diffuse β-AP deposits in the brain by synthetic β-AP antibodies. The immunoreactive β-AP deposits in skin were not detected by (or reacted very weakly with) the classical amyloid stains, Congo red and thioflavin S. Recently, Yamada, et al. reported that skin of AD patients does not show staining with Congo Red. *Acta Neuropathological* 77:136–141 (1988).

Example III

Observation in Living Patient

A 3 mm-diameter punch biopsy of skin from the forearm of an 85-year-old man with a six-year history of clinically typical AD was briefly fixed (30 minutes) in 10% neutral buffered formalin and examined immunohistochemically.

The skin sample was obtained with a punch biopsy bore from the inside of the forearm, under sterile technique following a small injection of local anaesthetic (1% lidocaine with epinephrine). Punch biopsies ranging in size from 3mm to 7mm diameter are generally suitable for this purpose. The biopsied sample included approximately 80% cutaneous and 20% subcutaneous tissue. The skin sample was fixed for about 30 minutes in 10% neutral buffered formalin. The sample was then removed from the formalin and placed in a physiological buffer (sodium phosphate buffered normal saline, pH 7.6, with 0.02% sodium azide) and stored at 4° C. The skin sample was then embedded in paraffin and sectioned in a microtome. Sections of approximately 5 to approximately 15 micrometers in diameter were mounted on glass microscope slides using a conventional histological adhering reagent.

After reaction with antiserum A (Table I) and a secondary goat anti-rabbit IgG antibody/avidin-biotin peroxidase detection system, this skin sample from a living patient showed readily detectable, specific β-AP immunostaining in the reticular dermis, when viewed through a brightfield light microscope. Using the panel of antibodies to native or synthetic β-AP (set forth in Table I), antibodies A, C and F produced moderate or strong staining of amorphous, apparently extracellular proteinaceous deposits having the histological characteristics described in Example II above for autopsied AD skin sections. Antibody Y produced mild to moderate staining. Abolition of the dermal staining by antibodies A, C and F occurred when these antisera were absorbed with a partially purified fraction of AD amyloid cores, whereas no change in the staining occurred when the absorption was carried out with a control brain function lacking amyloid cores. A similar abolition was obtained when antibody Y was absorbed with synthetic β-AP. Pretreatment (5–10 minutes) of the skin sections with concentrated (about 88%) formic acid abolished the β-AP immunoreaction. In order to insure that the β-AP deposits in the skin were being adequately immunoreacted, the sections were examined through the microscope to check the extent of the colorimetric reaction at frequent intervals during the final development step that uses DAB; as positive controls, simultaneously-stained sections of autopsied AD skin, previously proven to contain immunoreactive β-AP deposits, and autopsied AD brain were used.

As noted in Table I, the degree of β-AP detection was generally strongest when the skin sample was treated with antiserum A produced to β-AP antigen from AD cortex, and weakest when the sample was treated with antiserum L, produced to antigen from a synthetic $\beta_{1-28}$ peptide. However, the latter synthetic fragment of the β-AP (comprising amino acids 1–28) or smaller β-AP fragments of 8 or more amino acids, can be used as immunogens to produce peptide antibodies that can be used to detect skin β-AP deposits in AD patients. Various discrete regions of β-AP (or of a β-amyloid precursor protein fragment comprising β-AP) can serve as useful and specific antigens in the production of antibodies for immuno-detection of β-AP in skin.

A series of irrelevant hyperimmune sera to various antigens (listed in Table I and Example II) other than β-AP, as well as secondary antibody (goat anti-rabbit IgG) alone, produced no positive, specific staining of the β-AP-reactive deposits in the biopsied skin sample.

Example IV

Examination of Other Non-Neural Tissues

Certain other non-neural tissues of AD patients were examined immunocytochemically using one or more of the β-AP antibodies in Table I, as well as the unrelated control antisera. Deposits of β-AP-reactive material were detected in the submucosal connective tissue of the intestine in two neuropathologically confirmed AD patients, particularly in and around the walls of small blood vessels. Such vascular deposits were also found in the small intestine of an aged (77-year-old) patient without overt dementia, but whose brain showed many senile plaques characteristic of AD. Some of the immunoreactive material appeared to be localized extracellularly among connective tissue fibers. The vascular staining in the intestinal submucosa resembled the vascular and perivascular staining commonly seen in AD brain and meninges. This intestinal staining was markedly decreased or eliminated by absorption of the β-AP antibodies with AD brain amyloid cores, whereas absorption with an isolated fraction of control brain particles did not alter the reaction.

Immunochemical Examination Procedure for the Presence of β-AP Deposits in Intestine Sections of colon or small intestine obtained from patients who died with Alzheimer's Disease, with other neurological disorders, or of advanced age, were removed at autopsy and fixed in conventional fixatives (e.g., 10% neutral-buffered formalin). Following embedding of the sections in paraffin (or an alternative embedding medium), microscopic samples (i.e., sections) thereof were prepared using a microtome and placed on glass microscope slides. Following conventional deparaffinization and hydration of these samples by standard methods well-known in the art, the samples were contacted (reacted) with an antibody to either native or synthetic β-amyloid protein, as exemplified in Table I. For example, antibody A was used at 1:250 dilution in Tris-buffered or phosphate-buffered normal saline solution. This diluted primary antibody, or a control aliquot following absorption of the primary antibody with a form of the β-AP immunogen, was placed on the colon or intestine section and incubated for about 2-4 hours or overnight. Thereafter, the sections were washed with buffer and incubated with a secondary antibody reactive with the primary antibody, e.g., goat anti-rabbit IgG antibody. The secondary antibody was obtained commercially and had been coupled directly to biotin. This reaction was followed by washing the sections and then exposing them to a commercially obtained avidin-biotin complex coupled with peroxidase (Vector Laboratories, Burlingame, CA). Following this reaction, the reaction product was detected colorimetrically by incubation with 3, 3'-diamino-benzidine and hydrogen peroxide. The sample was viewed through a brightfield light microscope during the colorimetric reaction in order to determine the intensity of immunostaining, and therefore the proper duration, of this reaction. Thereafter, the sample was washed and dried, and a glass coverslip was mounted over the sample.

For analysis of immunoreactive β-AP in such immunostained intestinal sections, a slide was viewed in a standard light microscope using brightfield optics. Sections stained with the primary antibody were compared to an immediately adjacent section that had been stained with the primary antibody following its absorption with a β-AP immunogen. (For immunogens, see second column of Table I.) β-AP deposits in the colon were observed in the walls of small blood vessels and surrounding connective tissue in the submucosa. The brown immunoreaction product often resembled a serpentine cuff in the outer wall of the small blood vessel (e.g., arterioles). In the intestinal sections taken from two patients who died with autopsy-proven Alzheimer's disease, such vascular and perivascular submucosal colonic deposits were seen in both cases examined (see Table II). In intestinal sections taken from two patients dying with other disorders, only patients of advanced age (e.g., 77 years old or older) have thus far showed some intestinal submucosal blood vessels containing β-AP-immunoreactive deposits. Intestinal samples from patients under age 63 showed no perivascular β-AP deposits in these experiments.

In further immunohistochemical experiments on colonic and small intestinal tissues from AD and non-AD humans, each immunostained section was compared to a known positive colonic sample that had previously been identified as described above. Each new section was also compared to a known negative colonic sample so previously identified.

The location of the β-AP immuno reactive material in only selected vessels in this submucosal connective tissue of colon and small intestine made it easy to identify when viewed by light microscopy. In the β-AP-positive sections from AD subjects and certain aged normal patients, numerous intestinal blood vessels were devoid of β-AP reactivity whereas some contained peroxidase-positive (brown) immunoreactive deposits. Some immunoreactive β-AP deposits were also noted in the connective tissue surrounding blood vessels and in the deeper portion of mucosa.

In addition to the experiments just described, further experiments on sections of AD or non-AD intestine were performed using antibody Y (see Table I) at a dilution of 1:500, and antibodies C and F at dilutions of 1:250. Otherwise, the method was the same, and the same positive and negative controls were used in these experiments.

The results of the samples of intestine from AD and non-AD patients examined in the experiments described herein are exemplified in Table II.

Example V

Examination of Controls

Since some deposition of cerebrovascular and cerebral β-AP occurs commonly during normal aging, non-neural tissue samples were compared from 41 human subjects: eleven with AD, twenty-six without AD, and four with Trisomy 21 (Down's Syndrome) (Table II). All but four had been autopsied, establishing precise neurological diagnoses based on detailed neuropathological examinations. Eight of the eleven AD cases showed β-AP-reactive dermal deposits upon immunohistochemical staining. In contrast, none of fourteen non-demented subjects less than 63 years old showed βAP-immunoreactive material in skin. Of seven aged, neurologically diseased patients who did not have AD, four were negative and three were positive. Of five aged ($\geq 64$ year-old) normal subjects, three were negative, whereas two showed faintly staining, equivocal βAP-reactive material in skin. The deposits in the aged diseased and aged normal subjects had similar histological characteristics to those observed in the AD subjects, as described in Example II.

Example VI

Diagnostic Kit

The data in Table II demonstrate the diagnostic utility of this invention for AD. A kit for diagnosing Alzheimer's Disease can be prepared by separately packaging, for example, the following reagents (typical quantities and concentrations are listed for a 20-assay kit):

| Reagent | Quantity | Concentration | Source |
|---|---|---|---|
| Formalin | 5 mls | 10% | — |
| Antiβ-AP antibody | 5 mls | 10 mg/ml | murine monoclonal IgG |
| Anti-mouse IgG (with biotin label) | 5 mls | 50 μg/ml | goat |
| Avidin HRP | 5 mls | 0.5 μg/ml | — |
| Phosphate buffered saline | 25 mls | — | — |

The amounts and concentrations of reagents described herein can vary considerably depending on the specific application, as will be apparent to one of ordinary skill in the art.

Example VII

Quantitation of β-amyloid Reactivity in Skin or Other Non-Neural Tissues

A quantitative competitive immunoassay for β-AP reactivity can comprise the following: 1) a solid phase consisting of bound β-AP-containing material (e.g., native, purified β-AP or synthetic β-AP or β-AP filaments isolated from tissue) 2) a labeled anti-β-AP antibody and 3) a series of β-AP protein standards for production of a standard curve. Preferably, these components would be packaged in separate containers. The "label" on the antibody may be, for example, an enzyme (horseradish peroxide or alkaline phosphatase), fluorophore or radioisotope such as those typically used in the art.

A pre-determined amount of anti-β-AP antibody is preincubated with various concentrations of β-AP protein followed by incubation of the supernatant with the β-AP bound to the solid phase. Following detection of the bound label, a competitive standard curve will be generated and used to quantify the concentration of solubilized β-AP (or a fragment of β-AP comprising β-AP) in unknown skin (or other non-neural tissue) extracts.

This quantitative immunoassay may also be carried out using an extract or fine suspension of the skin sample without the β-AP actually being in solution (i.e., with the β-AP still in an insoluble form).

I claim:

1. A method of screening for Alzheimer's Disease, comprising the steps of:
   obtaining a skin tissue biopsy sample from a patient suspected of having Alzheimer's Disease;
   contacting at least a portion of the sample with a quantity of antibodies specific for β-amyloid protein, a β-amyloid precursor protein fragment comprising β-amyloid protein, or a peptide fragment of β-amyloid protein of at least about eight amino acids sufficient to allow detection of said protein, protein fragment or peptide fragment; and
   detecting the specific binding reaction of said antibodies with the skin tissue biopsy sample wherein the presence of said binding reaction is indicative of Alzheimer's disease.

2. The method of claim 1 wherein the antibodies are selected from the group of antibodies specific for β-amyloid protein and antibodies specific for a β-amyloid precursor protein fragment comprising β-amyloid protein.

3. The method of claim 2, wherein the β-amyloid protein and β-amyloid precursor protein fragment are isolated from a subject confirmed to have Alzheimer's Disease.

4. The method of claim 3, wherein the β-amyloid protein and β-amyloid precursor protein fragment are isolated from the cerebral cortex of said subject.

5. The method of claim 3, wherein the antibodies are selected from the group of antibodies specific for β-amyloid protein and antibodies specific for a β-amyloid precursor protein fragment comprising β-amyloid protein isolated from the skin of said subject.

6. The method of claim 2 further comprising prior to the contacting step, extracting β-amyloid protein from the sample and detecting the quantity of β-amyloid protein extracted from the sample through the specific binding reaction with said antibodies.

7. The method of claim 2, wherein detection of the specific binding reaction of said antibodies with the skin tissue biopsy sample is made microscopically by an immunohistochemical stain.

8. The method of claim 7 further comprising carrying out a control test comprising the additional steps of:
   pre-absorbing the antibodies with an excess amount of an antigen comprising β-amyloid protein;
   contacting a portion of the skin sample not previously contacted with antibodies or contacting a second skin sample from the same subject with the pre-absorbed antibodies; and detecting the presence of reaction between the portion of the skin sample or the second skin sample and the pre-absorbed antibodies wherein a decrease in the reaction of the pre-absorbed antibodies as compared to the sample tested initially indicates Alzheimer's disease.

9. The method of claim 3 where the antibodies are polyclonal.

10. The method of claim 3 where the antibodies are monoclonal.

11. A method for screening for Alzheimer's Disease, comprising the steps of:

obtaining a skin tissue biopsy sample from a patient suspected of having Alzheimer's Disease;

performing an extraction suitable for extracting β-amyloid protein, or a β-amyloid precursor protein fragment comprising β-amyloid protein, from the biopsy sample, and thereby obtaining an extract sample;

optionally additionally solubilizing the β-amyloid protein or the β-amyloid precursor protein fragment comprising β-amyloid protein present in the extract sample, and thereby obtaining a solution sample;

contacting the extract sample or the solution sample with a quantity of antibodies specific to β-amyloid protein or to a precursor protein fragment comprising β-amyloid protein or to a peptide fragment of β-amyloid protein of at least about eight amino acids sufficient to allow detection of said protein, protein fragment or peptide fragment; and detecting the specific binding reaction in the extract or solution sample between the antibodies and the β-amyloid protein or the β-amyloid precursor protein fragment comprising β-amyloid protein wherein the presence of said binding reaction is indicative of Alzheimer's disease.

12. The method of claim 11, wherein the antibodies are selected from the group of antibodies specific for β-amyloid protein and antibodies specific for a β-amyloid precursor protein fragment comprising β-amyloid protein isolated from a subject confirmed to have Alzheimer's Disease.

13. The method of claim 12, wherein the antibodies are specific for β-amyloid protein or β-amyloid precursor protein fragment isolated from the cerebral cortex of said subject.

14. The method of claim 12, wherein the antibodies are specific for β-amyloid protein or β-amyloid precursor protein fragment isolated from the skin of said subject.

15. The method of claim 11 where the antibodies are polyclonal.

16. The method of claim 11 where the antibodies are monoclonal.

17. The method of claim 1 where the antibodies are specifically immunoreactive with an epitope of the β-amyloid protein.

18. The method of claim 17 where the peptide fragment is synthetic.

19. The method of claim 18 where the antibodies are polyclonal.

20. The method of claim 18 where the antibodies are monoclonal.

* * * * *